United States Patent [19]

Zawacki

[11] Patent Number: 4,644,588
[45] Date of Patent: Feb. 24, 1987

[54] EYE SHIELD CAP FOR INFANTS

[75] Inventor: Edna M. Zawacki, Grosse Ile, Mich.

[73] Assignee: Alba Health Care, division of Alba-Waldensian, Inc., Valdese, N.C.

[21] Appl. No.: 871,467

[22] Filed: Jun. 6, 1986

[51] Int. Cl.⁴ .............................................. A61F 9/00
[52] U.S. Cl. ............................................. 2/10; 2/15;
2/201; 128/132 R; 128/163
[58] Field of Search .................... 2/10, 12, 2, 15, 172,
2/174, 201; 66/171, 169, 195; 128/132 R, 163

[56] References Cited

U.S. PATENT DOCUMENTS

| | | | |
|---|---|---|---|
| 945,839 | 1/1910 | Brisbane | 2/15 |
| 2,682,667 | 7/1954 | Michelstetter | 2/201 |
| 3,541,608 | 11/1970 | Otwell | 2/15 |
| 3,747,374 | 7/1973 | Meyer | 66/195 |
| 3,780,379 | 12/1973 | Kampman | 2/15 |
| 4,024,405 | 5/1977 | Szot | 2/15 |
| 4,411,263 | 10/1983 | Cook | 128/132 R |
| 4,502,476 | 3/1985 | Welt | 128/132 R |

Primary Examiner—Ronald Feldbaum
Attorney, Agent, or Firm—Bell, Seltzer, Park & Gibson

[57] ABSTRACT

This eye shield cap is formed of tubular knit stretchable open mesh fabric and includes a crown which snugly fits the head of the infant with a turned hem portion extending around the lower edge of the crown and adapted to extend behind the head and across the eyes of the infant. An elongate opaque fabric insert is positioned inside of the turned hem and extends across the area of the turned hem which covers the eyes and bridge of the nose of the infant. Lines of stitching extend along the turned hem and penetrate portions of the upper edge of the opaque fabric insert to retain the same in position. An upwardly curved bridge is formed in the medial portion of the lower edge of the elongate opaque fabric insert and is connected to the opaque fabric insert by additional stitching. The upwardly curved bridge portion serves to expose the upper portion of the nose of the infant to phototherapy treatment and the open mesh construction of the crown also exposes the head of the infant to the phototherapy treatment light rays.

3 Claims, 6 Drawing Figures

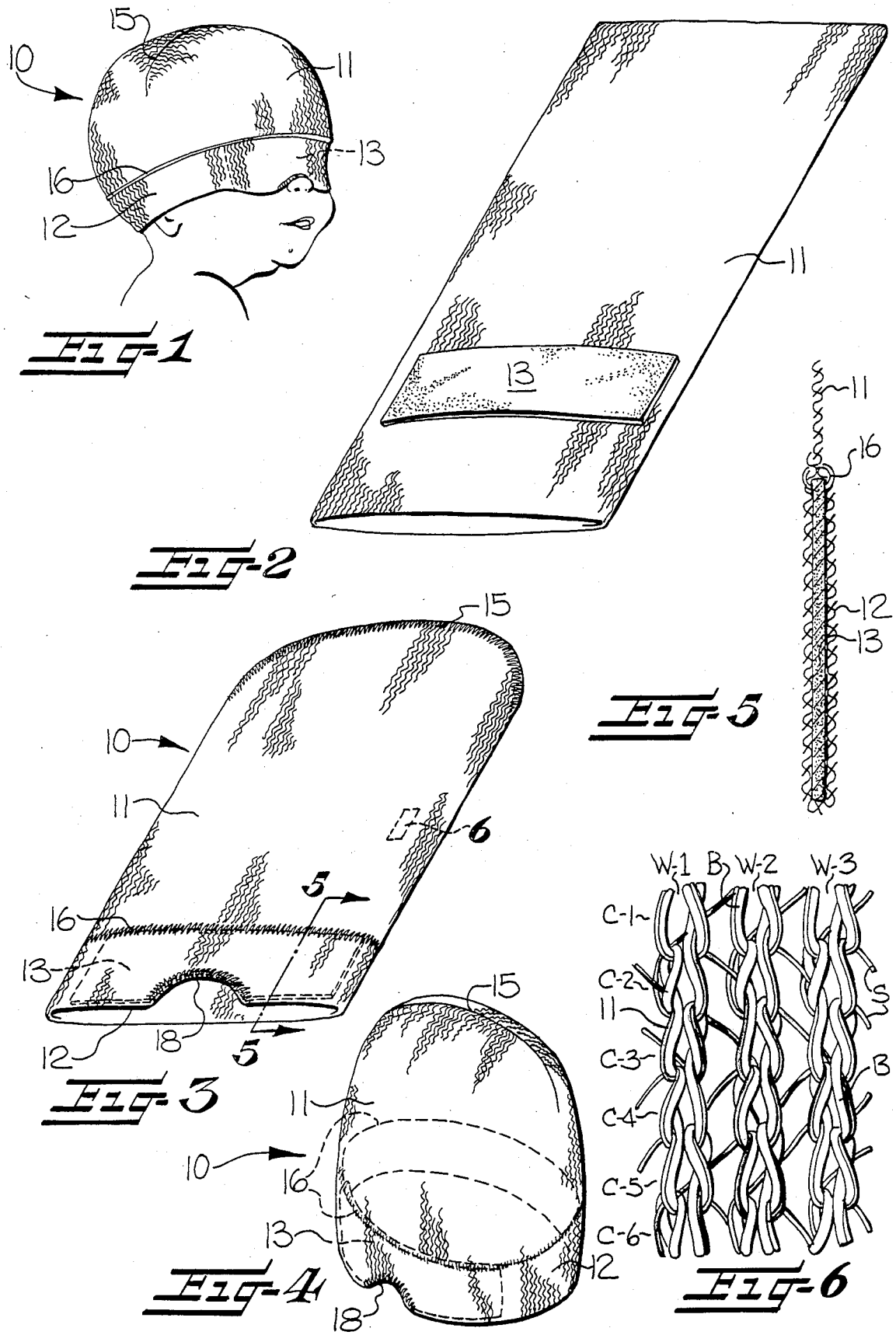

EYE SHIELD CAP FOR INFANTS

FIELD OF THE INVENTION

This invention relates generally to an eye shield cap for wear by newborn infants requiring phototherapy treatment, and more particularly to such a cap which is formed of stretchable open mesh knit fabric and including a turned hem extending across the eyes of the infant with an opaque fabric insert fixed in position in the turned hem and covering and protecting the eyes of the infant.

BACKGROUND OF THE INVENTION

In some cases, it is necessary to subject newborn infants to phototherapy treatment with strong light rays to counteract various illnesses, such as bilirubinemia, and these strong light rays may injure the eyes of the infant, if not protected. U.S. Pat. No. 3,541,608 discloses an eye shield for protecting the eyes of the infant during such phototherapy treatment. The eye shield of this patent is formed of a series of interconnected strap members secured to an encircling band which extends around the head and across the eyes of the infant and is connected together at opposite ends by Velcro fasteners with the straps extending across the head of the infant and beneath the chin. While the eye shield of this patent does protect the eyes of the infant from the strong light rays, it requires some skill and careful positioning of the eye shield over the eyes of the infant. Also, the straps and encircling band prevent the light rays from contact with the skin in those areas in which it covers and the straps and band may chafe and irritate the skin of a newborn infant.

U.S. Pat. No. 4,411,263 also discloses an eye shield for protecting the eyes of an infant during phototherapy treatment. The eye shield of this patent provides a narrow strip of opaque material extending across the eyes and the bridge of the nose of the infant and being removably connected at opposite ends to adhesive tabs positioned on the temples of the infant. The removable connection between the opposite ends of the narrow eye shielding strip and the adhesive tabs is illustrated in the form of Velcro fasteners. While the eye shield of this patent does provide maximum skin exposure while protecting the eyes of the infant, the adhesive attachment of the adhesive tabs to the temples of the infant may cause irritation and allergic reaction. Also, the long strip material extending across the eyes and bridge of the nose of the infant may become displaced and will not effectively cover and protect the infant's eyes.

SUMMARY OF THE INVENTION

With the foregoing in mind, it is an object of the present invention to provide an eye shield cap for infants which is formed of stretchable open mesh fabric adapted to snugly fit the head of the infant and provide exposure to the skin by the light rays during treatment, and including an elongate opaque fabric insert positioned in the lower turned hem portion of the cap for extending across and covering the eyes of the infant during such treatment.

The eye shield cap of the present invention has sufficient stretchability to snugly fit a range of infants having slightly different head sizes and is manufactured in several sizes so as to fit the head of infants of different sizes. The cap fits the head with sufficient snugness that the cap will remain in position, and yet will not be uncomfortably tight on the head of the infant.

The eye shield cap of the present invention is formed of a tubular knit sleeve of fabric and the upper crown is formed by a transverse closure seam while the lower opening is formed by turning the tubular knit fabric upon itself and forming a line of stitching to provide a turned hem portion therearound. An opaque fabric insert is positioned inside of the turned welt and extends across the area of the turned welt which is adapted to cover the eyes of the infant. Stitching extends along the turned welt and penetrates one edge portion of the opaque fabric insert to retain the same in position therein. An upwardly curved bridge is formed in the medial portion of the lower edge of the elongate opaque fabric insert in the hem and includes further stitching extending along the curved bridge portion and penetrating the lower edge of the turned hem to provide exposure for the upper portion of the nose of the infant. The tubular knit fabric forming the stretchable open mesh cap or crown portion is preferably warp knit and includes a plurality of walewise stitch chains of stretchable textured yarn extending from the closed top of the crown of the cap and throughout the turned welt portion. Elastic yarn stitch chains are interknit with the stretchable textured yarn stitch chains and provide diagonally extending laps extending between and interconnecting the stitch chains to provide both walewise and coursewise stretchability to the fabric and to provide the open mesh structure thereto.

BRIEF DESCRIPTION OF THE DRAWINGS

Other objects and advantages will appear as the description proceeds when taken in connection with the accompanying drawings, in which FIG. 1 illustrates the eye shield cap of the present invention positioned on the head of a newborn infant;

FIG. 2 is a perspective view illustrating a length of tubular knit open mesh fabric, and showing the first step in forming the eye shield cap;

FIG. 3 is a view similar to FIG. 2 but showing a further step in forming the eye shield cap;

FIG. 4 is a view similar to FIG. 3 but showing the cap everted to the right-side-out condition;

FIG. 5 is an enlarged, somewhat schematic, view taken substantially along the line 5—5 in FIG. 3; and FIG. 6 is a greatly enlarged view of a fragmentary portion of the tubular knit sleeve and showing the particular warp knit construction thereof.

DESCRIPTION OF THE ILLUSTRATED EMBODIMENT

As illustrated in FIG. 1, the eye shield cap, broadly indicated at 10, includes a crown portion 11 shaped to cover and snugly fit the head of the infant, and a turned hem 12 extending around the open lower edge of the crown 11 and adapted to extend behind the head and across the eyes and bridge of the nose of the infant. An elongate opaque fabric insert 13 is positioned inside of the turned hem 12 and covers the eyes of the infant. Stitching means, to be presently described, extends along the inner edge of the turned hem 12 and penetrates the upper edge of the opaque fabric insert 13 to retain the same in position in the turned hem 12.

As illustrated in FIGS. 2 and 3, the eye shield cap 10 is formed from a tubular knit sleeve of stretchable open mesh fabric and the upper open end is closed by a curved closure seam 15 (FIG. 3) which forms the closed upper crown 10 of the cap. The closure seam 15 is preferably of the overedge type and the fabric is trimmed along the curved line as the seam 15 is formed. The opaque fabric insert 13 is preferably formed of felt fabric and is initially in the form of an elongate rectangle, as illustrated in FIG. 2. The insert 13 is positioned on and extends partially around the tubular knit open mesh sleeve.

The lower open end of the knit sleeve is then turned upwardly over the opaque fabric insert 13 and a line of stitching 16 (FIG. 3) is formed around the cap and connects the free end of the sleeve to the body of the cap to form the turned hem portion 12 and to also connect the upper edge of the elongate opaque fabric insert 13 to the upper edge of the turned hem 12. The line of stitching 16 is also preferably of the overedge seam type so that the stretchability of the open mesh fabric is not restricted.

A curved overedge seam 18 is then formed along the lower edge of the turned hem 12 and in the medial portion of the elongate opaque insert 13, as illustrated in FIG. 3, to provide an upwardly curved bridge formed in the medial portion of the lower edge of the opaque insert 13 to expose the upper portion of the nose of the infant and to assure proper positioning of the cap on the head of the infant. The formation of the curved seam 18 trims away and penetrates the lower edge of the turned hem 12 and also trims away and penetrates the opaque fabric insert 13 to form an upwardly curved bridge portion. The curved bridge portion aids in maintaining the fabric insert 13 in the proper position in the turned hem 12.

While the present eye shield cap can be knit of various types of open mesh fabric, it is preferred that the tubular sleeve be warp knit and that it be stretchable in both longitudinal and circumferential directions so that it snugly fits the head of the infant. The preferred construction of the warp knit open mesh fabric is illustrated in detail in FIG. 6 and includes a plurality of walewise spaced-apart stitch chains knit of stretchable textured yarn B, as illustrated in wales W-1, W-2 and W-3, and extending from the closed top of the crown portion 11 and throughout the turned hem 12. The body yarns B are preferably textured synthetic stretchable yarns and the individual stitch chains are connected together by elastic yarn, such as covered spandex yarns, indicated at S. The yarns S form stitch chains interknit with the stretchable textured yarn stitch chains of the body yarn B and form diagonally extending laps extending between and interconnecting the stitch chains to provide both walewise and coursewise stretchability to the knit fabric.

As illustrated in FIG. 6, each of the covered spandex yarns S is shogged or lapped a distance of two wales in one direction and then lapped in the reverse direction a distance of two wales. For example, it will be noted in FIG. 6 that the covered spandex yarn S which forms a stitch loop in course C-2 of wale W-1 extends downwardly and diagonally to the right and forms the next stitch loop in course C-3 of wale W-2. The spandex yarn S then extends downwardly and diagonally to the right and forms the next stitch loop in course C-4 of wale W-3. The spandex yarn then reverses direction and is shogged to the left so that it extends downwardly and diagonally to form the next stitch loop in course C-5 of wale W-2, and then extends downwardly and diagonally to form the next stitch loop in course C-6 of wale W-1.

The opaque fabric insert 13 extends less than one-half the distance around the circumference of the turned hem 12 and is attached and held in position along its upper edge portion by the stitching 16 forming the hem 12. Since the opaque fabric insert 13 is primarily nonstretchable, it does limit the stretchability of the portion of the cap which extends across the eyes of the infant. However, the insert 13 does not limit the stretchability of the cap to the extent that it does not snugly fit the head of the infant.

The cap of the present invention may be easily drawn over the head of the infant and the opaque fabric insert is positioned across the eyes to cover and protect them during phototherapy treatment. The open mesh construction of the knit fabric forming the crown of the cap is sufficiently open and porous to admit the treatment light rays and the cap is produced at a sufficiently low cost that it can be discarded after use. The cap is preferably packaged in a sterile package and may be removed therefrom and immediately placed on the head of the infant to receive the phototherapy treatment.

In the drawings and specification there has been set forth the best mode presently contemplated for the practice of the present invention, and although specific terms are employed, they are used in a generic and descriptive sense only and not for purposes of limitation, the scope of the invention being defined in the claims.

That which is claimed is:

1. An eye shield cap for protecting an infant's eyes from phototherapy treatment light and comprising
   a crown portion of tubular knit stretchable open mesh fabric shaped to cover and snugly fit the head of the infant,
   a turned hem portion intregal with and extending around the open lower edge of said crown and adapted to extend behind the head and across the eyes of the infant, said turned hem being formed by turning the tubular knit fabric upon itself,
   an elongate opaque fabric insert positioned inside of said turned hem and extending across the area of the turned hem covering the eyes of the infant, and
   stitching means extending along and around said turned hem and penetrating said opaque fabric insert to retain the same in position in said turned hem, and connecting the upturned hem portion to said crown portion.

2. An infant eye shield cap according to claim 1 wherein said knit fabric is warp knit and includes a plurality of walewise stitch chains of stretchable textured yarn extending from the closed top of said crown portion and throughout said turned hem portion, and elastic yarn stitch chains interknit with said stretchable textured yarn stitch chains and providing laps extending between and interconnecting said stitch chains to provide both walewise and coursewise stretchability to the knit fabric.

3. An infant eye shield cap according to claim 1 including an upwardly curved bridge formed in the medial portion of the lower edge of said elongate opaque fabric insert, and including further stitching means extending along said upwardly curved bridge portion and penetrating the lower edge of said turned hem to expose the upper portion of the nose of the infant.

* * * * *